United States Patent
Mattson et al.

(10) Patent No.: US 6,350,877 B1
(45) Date of Patent: Feb. 26, 2002

(54) MANUFACTURING PROCESS

(75) Inventors: Anders Mattson, Täby; Carina Svensson; Karin Thörnblom, both of Södertälje; Christina Ödman, Mariefred, all of (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/508,260

(22) PCT Filed: Nov. 22, 1999

(86) PCT No.: PCT/SE99/02155

§ 371 Date: Mar. 8, 2000

§ 102(e) Date: Mar. 8, 2000

(87) PCT Pub. No.: WO00/31035

PCT Pub. Date: Jun. 2, 2000

(51) Int. Cl.$^7$ .................. C07D 213/80; C07D 213/803; A61K 31/44

(52) U.S. Cl. .................. 546/322; 546/321; 514/356

(58) Field of Search .................. 546/321, 322; 514/356

(56) References Cited

U.S. PATENT DOCUMENTS

| | | | |
|---|---|---|---|
| 4,446,317 A | 5/1984 | Gregson et al. | 544/22 |
| 5,739,152 A | * 4/1998 | Andersson et al. | 514/356 |
| 5,856,346 A | * 1/1999 | Andersen et al. | 514/356 |

FOREIGN PATENT DOCUMENTS

WO      9512578      5/1995

* cited by examiner

*Primary Examiner*—Alan L. Rotman
(74) *Attorney, Agent, or Firm*—White & Case LLP

(57) ABSTRACT

A method for the manufacture of clevidipine by reaction of an inorganic salt of 4-(2',3'-dichlorophenyl)-1,4-dihydro-5-methoxycarbonyl-2,6-dimethyl-3-pyridine-carboxylate and chloro methyl butyrate.

12 Claims, No Drawings

MANUFACTURING PROCESS

This application is a 371 of PCT/SE99/02155 filed Nov. 22, 1999.

FIELD OF THE INVENTION

The present invention relates to an improved method for the manufacture of clevidipine (butyroxymethyl methyl 4-(2',3'-dichlorophenyl)-2,6-dimethyl-1,4-dihydropyridine-3,5-dicarboxylate) via the route of reacting 4-(2',3'-dichlorophenyl)-1,4-dihydro-5-methoxycarbonyl-2,6-dimethyl-3-pyridinecarboxylic acid with chloromethyl butyrate.

PRIOR ART

WO 95/12578 discloses a method for the preparation of clevidipine using as reactants 4-(2',3'-dichlorophenyl)-1,4-dihydro-5-methoxycarbonyl-2,6-dimethyl-3-pyridinecarboxylic acid. The disclosed method has several drawbacks.

DISCLOSURE OF THE INVENTION

It has now been found that clevidipine, which is a short-acting calcium-channel blocker, can be prepared in a manner that is faster, reduces the amount of byproducts, is more environmentally sound and gives a better yield than the process disclosed in WO 95/12578. It also increases the stability of one of the intermediates allowing it to be isolated and stored without drying.

The method according to the invention uses an inorganic salt instead of the neutral form of carboxylic acid.

The method which is schematically outlined below is characterized by reaction of compound A, wherein $A^+$ is a positively charged inorganic ion with chloromethyl butyrate to obtain clevidipine.

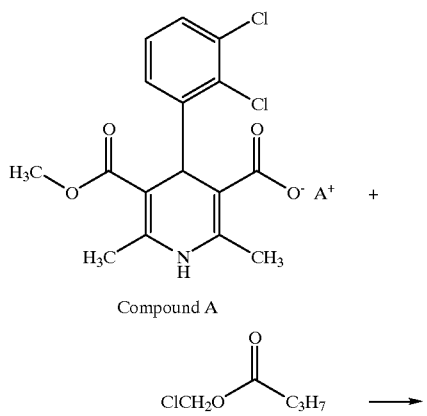

Compound A

Chloro methyl butyrate

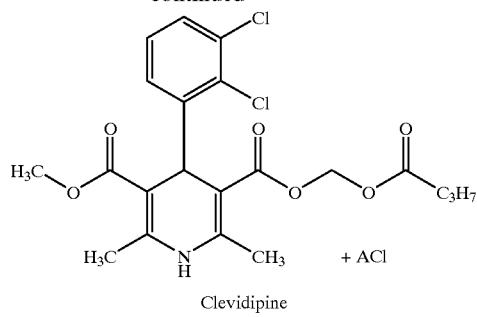

Clevidipine

Compound A is reacted with chloromethyl butyrate optionally in the presence of a corresponding hydrogen carbonate (preferable $KHCO_3$) in refluxing acetonitrile. $A^+$ is preferably potassium or sodium, most preferably potassium. Preferably the inorganic salts are removed by filtration and the product is crystallized. The crystallization can be performed for instance by the addition of isopropanol and water with subsequent cooling. It can also be crystallized by exchanging solvent from acetonitrile to a mixture of alcohol, such as ethanol or isopropanol, preferably ethanol, and water with repeated evaporations. In the further purification of the product the crystals are washed with a mixture of water and ethanol or isopropanol. The product can be dissolved in refluxing isopropanol, crystallized by cooling, isolated by filtration and finally washed with a water and isopropanol mixture.

In a preferred embodiment Compound A is reacted with chloromethyl butyrate (1.2–2.8 eq., preferably 1.4–1.6 eq.). The reactants are charged together with potassium hydrogen carbonate (1.5–0.4 eq., preferable 0.8–0.6 eq.) and the solvent acetonitrile (3–12 ml/g of Compound A).

Preparation of Compound A starting material

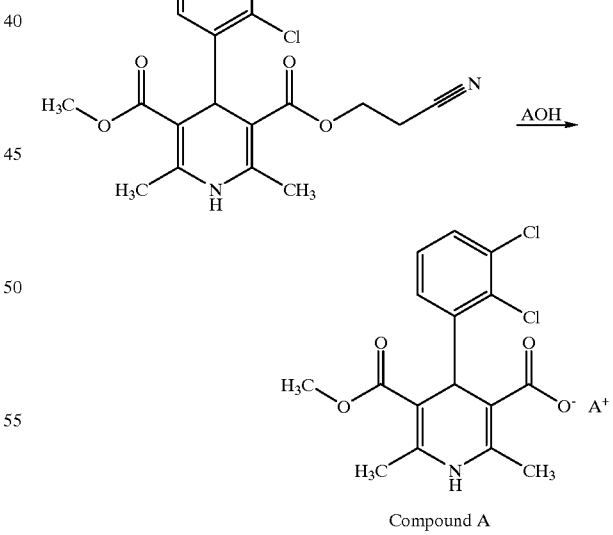

Compound A

Cyanoethyl methyl 4-(2',3'-dichlorophenyl)-2,6-dimethyl-1,4-dihydropyridine-3,5-dicarboxylate is reacted with potassium hydroxide or other suitable hydroxide e.g. sodium hydroxide in isopropanol over night at room temperature. Some of the solvent can be evaporated off to increase the yield or the product is isolated direct without any evaporation and washed with isopropanol.

WORKING EXAMPLES

Example 1

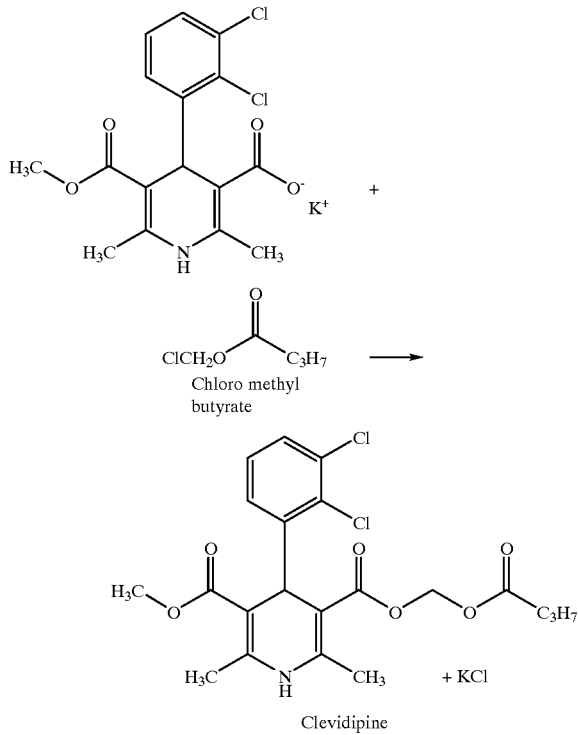

Clevidipine

Potassium 4-(2',3'-dichlorophenyl)-1,4-dihydro-5-methoxycarbonyl-2,6-dimethyl-3-pyridinecarboxylate (10.6 kg 27 mol; 1 eq), acetonitrile (63 L) and chloromethyl butyrate (5.8 kg ,42 mol; 1.6 eq) were heated to reflux. After 3.5 h at reflux the inorganic salts were filtered off and washed with warm acetonitrile (25 L). The temperature of the solution was adjusted to 50° C. and then 2-propanol (17 kg) and water (110 kg) were added to the solution. The slurry was left over night (8.5 h) at 25° C. before the product was isolated and washed with a mixture of 2-propanol (16 kg) and water (28 kg). This gave clevidipine-crude (11.0 kg, 90%) as a white to slightly yellowish solid. LC-purity 99.58%, LC-assay 98.93% (w/w)

Example 2

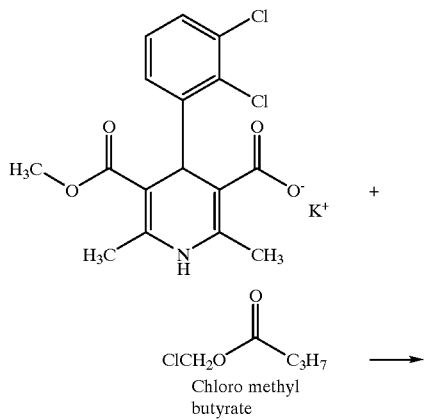

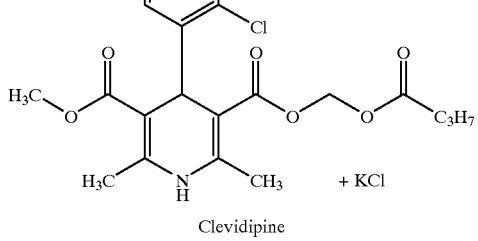

Clevidipine

Potassium 4-(2',3'-dichlorophenyl)-1,4-dihydro-5-methoxycarbonyl-2,6-dimethyl-3-pyridinecarboxylate (6.7 g, 15 mmol; 1 eq), KHCO₃ (0.9 g, 9 mmol; 0.6 eq), acetonitrile (50 ml) and chloromethyl butyrate (2.7 ml, 21 mmol; 1.4 eq) were heated to reflux. After 4.5 h at reflux the inorganic salts were filtered off and washed with warm acetonitrile (20 ml). The solvent was exchanged from acetonitrile to ethanol:water (~35 ml, 2:1). The solution was left over night (17 h) at ambient temperature before the product was isolated and washed with a mixture of ethanol:water (3*5 g, 3:1). This gave clevidipine-crude (5.2 g, 76%) as a white to slightly yellowish solid. LC-purity 99.2

Example 3

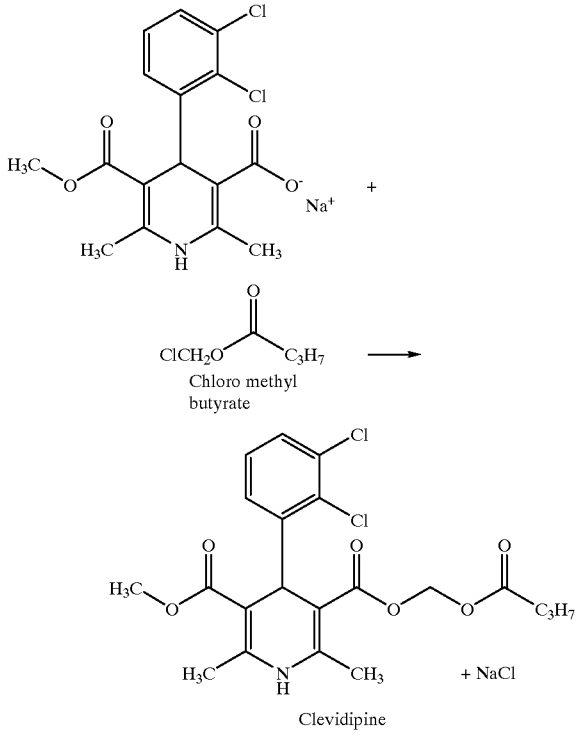

Clevidipine

Sodium 4-(2',3'-dichlorophenyl)-1,4-dihydro-5-methoxycarbonyl-2,6-dimethyl-3-pyridinecarboxylate (7.0 g, 15 mmol; 1 eq), NaHCO₃ (0.8 g, 9 mmol; 0.6 eq), acetonitrile (50 ml) and chloromethyl butyrate (2.7 ml , 21 mmol; 1.4 eq) were heated to reflux. After 5 h at reflux the inorganic salts were filtered off and washed with warm acetonitrile (20 ml). The solvent was exchanged from acetonitrile to ethanol:water (~35 ml, 2:1). The solution was left over night (17 h) at ambient temperature before the product was isolated and washed with a mixture of ethanol:water (3*5 g, 3:1). This gave clevidipine-crude (5.1 g, 74%) as a white to slightly yellowish solid. LC-purity 98.8%

Example 4

Clevidipine crude (7.5 g, 16 mmol) and 2-propanol (38 g) were heated to reflux. The temperature was adjusted to 40° C. and water (48 g) was added. The solution was left over night at ambient temperature before the product was isolated and washed with a mixture of 2-propanol:water (2*10 g (45:55% w/w)). This gave clevidipine (7.2 g, 96%) as a white to slightly off white solid. LC-purity 99.9%

What is claimed is:

1. An improved method for the manufacture of clevidipine, comprising mixing a compound of the formula I,

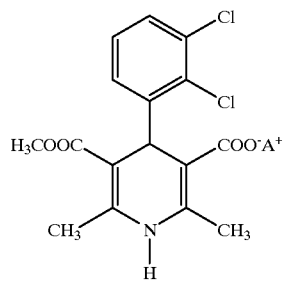

I wherein $A^+$ is an inorganic cation such that the compound is in salt form, with a solvent to form a mixture substantially free of the free acid of the compound, and reacting the compound of formula I with chloromethyl butyrate.

2. The method according to claim 1, wherein the reaction is performed in the presence of $A^+HCO_3$, wherein $A^+$ is an inorganic cation.

3. The method according to claim 1, wherein the reaction is performed in acetonitrile.

4. The method according to claim 3, wherein the reaction is performed in refluxing acetonitrile.

5. The method according to claim 1, wherein $A^+$ is a potassium or sodium ion.

6. The method according to claim 1, wherein $A^+$ is a potassium ion.

7. The method according to claim 2, wherein $A^+$ is a potassium ion and the corresponding hydrogen carbonate is potassium hydrogen carbonate.

8. The method according to claim 1, wherein the obtained clevidipine is purified by crystallization.

9. The method according to claim 8, wherein the obtained clevidipine is crystallized by the addition of isopropanol and water with subsequent cooling.

10. The method according to claim 1, wherein the molar ratio between the compound of formula I and chloromethyl butyrate in the initial reaction mixture is 1:1.2–2.8.

11. A method for the manufacture of clevidipine in the form of a pharmaceutical preparation wherein clevidipine is produced according to any of the preceding claims and thereafter purified clevidipine is admixed with an excipient, diluent or carrier to provide the pharmaceutical preparation.

12. The method of claim 1, wherein the clevidipine produced is substantially free of the free acid of the compound.

* * * * *